United States Patent
Katayama et al.

[11] Patent Number: 6,034,190
[45] Date of Patent: Mar. 7, 2000

[54] OLEFIN POLYMERIZATION CATALYST COMPONENT

[75] Inventors: Hiroaki Katayama; Masaaki Nabika; Akio Iami, all of Ichihara; Norio Kawamura, Chiba; Hidenori Hanaoka, Osaka, all of Japan

[73] Assignee: Sumitomo Chemical Company, Limited, Osaka, Japan

[21] Appl. No.: 09/122,107

[22] Filed: Jul. 24, 1998

Related U.S. Application Data

[62] Division of application No. 08/695,382, Aug. 9, 1996, Pat. No. 5,840,646.

[30] Foreign Application Priority Data

Aug. 11, 1995 [JP] Japan ..................... 7-205953

[51] Int. Cl.$^7$ .............. C08F 4/44; C08F 210/00
[52] U.S. Cl. .................. 526/127; 526/132; 526/153; 526/160; 526/161; 526/348
[58] Field of Search .................. 526/127, 132, 526/153, 160, 161

[56] References Cited

U.S. PATENT DOCUMENTS

| | | | |
|---|---|---|---|
| 3,502,640 | 3/1970 | Shuto et al. | 502/152 |
| 3,505,369 | 4/1970 | Deffner | 502/152 |
| 3,737,416 | 6/1973 | Hayashi et al. | 526/153 |
| 3,856,839 | 12/1974 | Smith et al. | 556/54 |
| 4,452,914 | 6/1984 | Coleman, III et al. | 526/125 |
| 4,933,456 | 6/1990 | Rocklage et al. | 534/15 |
| 5,223,465 | 6/1993 | Ueki et al. | 526/160 |
| 5,527,752 | 6/1996 | Reichle et al. | 526/160 |
| 5,629,391 | 5/1997 | Cardi et al. | 526/161 |
| 5,629,392 | 5/1997 | Santi et al. | 526/160 |
| 5,728,641 | 3/1998 | Aida et al. | 526/132 |
| 5,750,456 | 5/1998 | Dossett | 502/155 |
| 5,756,610 | 5/1998 | Tsai et al. | 526/161 |
| 5,840,646 | 11/1998 | Katayama et al. | 502/152 |

FOREIGN PATENT DOCUMENTS

| | | |
|---|---|---|
| 0241235 | 10/1987 | European Pat. Off. . |
| 0241560 | 10/1987 | European Pat. Off. . |
| 5230133 | 9/1993 | Japan . |
| 6192330 | 7/1994 | Japan . |
| 2 224 735 | 5/1990 | United Kingdom ............ 556/56 |

OTHER PUBLICATIONS

Chemical Abstracts, 87:67592 (1977).

*Primary Examiner*—Mark L. Bell
*Assistant Examiner*—J. Pasterczyk
*Attorney, Agent, or Firm*—Birch, Stewart, Kolasch & Birch, LLP

[57] ABSTRACT

An olefin polymerization catalyst component is represented by the general formula (1):

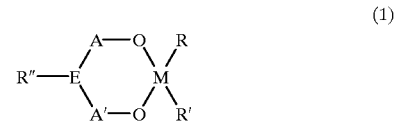

(1)

wherein M is a transition metal of the 4$^{th}$ Group or the Lanthanide Series in the Periodic Table; each of A and A' is the same or different and is a hydrocarbon or halogenated hydrocarbon having 1 to 50 carbon atoms, or a hydrocarbon or halogenated hydrocarbon group having 1 to 50 carbon atoms and a substituent containing an oxygen atom; E is a residual group of an element of the 13th to 15th Groups capable of forming three bonds; each of R and R' is the same or different and is a halogen atom or a hydrocarbon group having 1 to 20 carbon atoms; R" represents a hydrocarbon or halogenated hydrocarbon group containing at least one hetero atom and having 1 to 20 carbon atoms. This component is used in a catalyst along with an aluminum or born-containing cocatalyst to produce an olefin polymer or copolymer.

4 Claims, No Drawings

OLEFIN POLYMERIZATION CATALYST COMPONENT

This application is a divisional of application Ser. No. 08/695,382, filed on Aug. 9, 1996, now U.S. Pat. No. 5,840,646 the entire contents of which are hereby incorporated by reference.

BACKGROUND OF THE INVENTION

1. Field of the Invention

The present invention relates to an olefin polymerization catalyst component, an olefin polymerization catalyst and a process for producing an olefin polymer. In more particular, the present invention relates to a process for producing an olefin polymer, particularly a linear low density polyethylene by using a transition metal complex having a cyclic structure where two oxygen atoms are bonded with the transition metal atom and further containing a hetero atom in a substituent not contained in the cyclic structure as a main catalyst component for the polymerization of olefins.

2. Prior Art

Many reports have been already published about methods for producing an olefin polymer with a metallocene complex. For example, in Japanese Unexamined Patent Publication Sho No.58-19309, a process for producing an olefin polymer with a metallocene complex and an aluminoxane is reported. However, there was a problem in that the molecular weight of the olefin polymer obtained was low when an olefin was polymerized with the system using bis(cyclopentadienyl) zirconium dichloride and methylaluminoxane.

To address this problem, in WO Publication No. 87/02370, the usage of a reaction product of an organic compound having at least two hydroxy groups with a transition metal compound is reported. But, in the system using 2,2'-thiobis(6-tert-butyl-4-methylphenoxy)titanium dichloride and methylaluminoxane in the report, there was a problem in that although its molecular weight was properly high at an advantageous reaction temperature in an industrial process, the activity was low.

In Japanese Unexamined Patent Publication Hei No. 5-230133, a process for polymerizing propylene or ethylene by using 2,2'-thiobis(6-tert-butyl-4-methylphenoxy)titanium dichloride, triisobutylaluminum and triphenylmethyltetrakis(pentafluorophenyl)borate is disclosed, but the polymerization temperature is too low from the viewpoint of an industrial process.

On the other hand, in Japanese Unexamined Patent Publication Hei No.6-192330, there is disclosed a process for copolymerizing ethylene with an α-olefin at 80° C. with 2,2'-thiobis(6-tert-butyl-4-methylphenoxy)titanium dichloride, triisobutylaluminum and dimethylaniliniumtetrakis(pentafluorophenyl)borate, but there was a problem in that a large amount of triisobutylaluminum was used.

SUMMARY OF THE INVENTION

An object of the present invention is to provide a new catalyst component for polymerizing an olefin exibiting a high activity at an advantageous reaction temperature in an industrial process.

Another object of the present invention is to provide a catalyst which allows for the reduction of the amount used of the organoaluminum component possible and priorities for the production of an olefin polymer with a high molecular weight.

Other objects and advantages of the present invention will be apparent from the description below.

The present inventors have intensively studied olefin polymerization catalyst components and a catalyst using these components. As a result, the present inventors found a transition metal complex having a cyclic structure where two oxygen atoms are bonded with the transition metal and further containing a hetero atom in a substituent not contained in the cyclic structure as a catalyst component for polymerizing an olefin, and completed the present invention.

That is, the present invention provides an olefin polymerization catalyst component represented by the general formula (1):

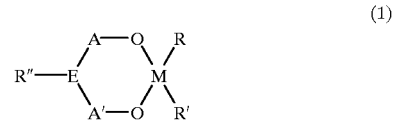

(wherein M is a transition metal of the 4th Group or the Lanthanide Series in the Periodic Table. O is an oxygen atom. Each of A and A' is a hydrocarbon or halogenated hydrocarbon group having 1 to 50 carbon atoms, or a hydrocarbon or halogenated hydrocarbon group having a substituent containing an oxygen atom, and having 1 to 50 carbon atoms, and A and A' may be the same or different. E is the residual group of the 13th to 15th Groups capable of forming three bonds.)

Each of R and R' is a halogen atom or a hydrocarbon group having 1 to 20 carbon atoms and R and R' may be the same or different. R" represents a hydrocarbon or halogenated hydrocarbon group containing at least one or more of hetero atoms and having 1 to 20 carbon atoms. In the above formula, O represents an oxygen atom.

Moreover, the present invention provides an olefin polymerization catalyst comprising using said catalyst component above and at least one compound (A) selected from an organoaluminum compound indicated by the general formula $R^1{}_a AlZ_{3-a}$ (A1), a cyclic aluminoxane having a structure indicated by the general formula $\{-Al(R^2)-O-\}_b$ (A2) and a linear aluminoxane having a structure indicated by the general formula $R^3(R^3-Al-O)_c AlR^2{}_2$ (A3), wherein each of $R^1$, $R^2$ and $R^3$ is a hydrocarbon group having 1 to 8 carbon atoms, and in the above-mentioned general formulae all of $R^2$, all of $R^2$ and all of $R^3$ may be the same or different. Z represents a hydrogen or halogen atom and 2 or more kinds of Zs may be contained in the molecule. a is a number satisfying $0<a\leq 3$, b represents an integer of 2 or more, and c represents an integer of 1 or more.

Further, the present invention provides a process for producing an olefin polymer with said catalyst.

The present invention is explained in detail below.

DETAILED DESCRIPTION OF THE INVENTION

In the catalyst component for polymerizing an olefin represented by the above-mentioned general formula (1), M is a transition metal element of the 4th Group or the Lanthanide Series of the Periodic Table of the Elements (the revised edition of IUPAC nomenclature of inorganic chemistry, 1989), and examples include a titanium atom, a zirconium atom, a hafnium atom, a samarium atom and the like. A titanium atom, a zirconium atom or a hafnium atom is preferred.

Each of A and A' in the above-mentioned general formula (1) is a hydrocarbon or halogenated hydrocarbon group having 1 to 50 carbon atoms, or a hydrocarbon or halogenated hydrocarbon group having a substituent containing an oxygen atom and 1 to 50 carbon atoms. Examples of A and A' include, for example, an alkylene group(formula(2)), a vinylene group(formula(3)), a phenylene group (formula (4)), a naphthalene group(formula(5)) represented by the following general formulae (2)-(5), and any combinations thereof, but they are not restricted thereto.

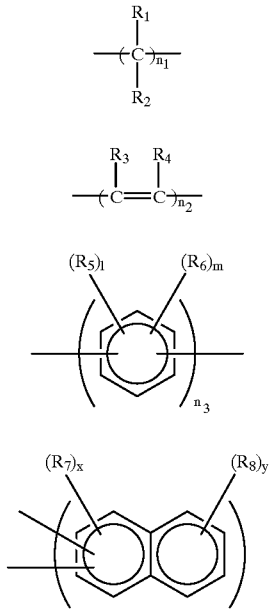

Each of $R_1$, $R_2$, $R_3$, $R_4$, $R_5$, $R_6$, $R_7$ and $R_8$ is a hydrogen atom, a hydrocarbon or halogenated hydrocarbon group having 1 to 20 carbon atoms, a hydrocarbon group having a substituent containing oxygen, and having 1 to 20 carbon atoms or a halogen atom, and they may be the same or different. Each of $n_1$, $n_2$, $n_3$ and $n_4$ is an integer of 1 to 5, preferably 1 to 3, more preferably 1. Each of 1 and m is an integer of 0 to 4 satisfying $0 \leq 1+m \leq 4$, x is an integer of 0 to 2, and y is an integer of 0 to 4.

As examples of $R_1$, $R_2$, $R_3$, $R_4$, $R_5$, $R_6$, $R_7$ and $R_8$, hydrocarbon groups include methyl, ethyl, n-propyl, isopropyl, n-butyl, isobutyl, sec-butyl, tert-butyl, n-pentyl, neopentyl, n-hexyl, n-octyl, phenyl, 2-methylphenyl, 3-methylphenyl, 4-methylphenyl, 2,3-dimethylphenyl, 2,4-dimethylphenyl, 2,5-dimethylphenyl, 2,6-dimethylphenyl, 2,3,4-trimethylphenyl, 2,3,5-trimethylphenyl, 2,3,6-trimethylphenyl, 2,3,4,5-tetramethylphenyl, 2,3,4,6-tetramethylphenyl, pentamethylphenyl, a fluoromethyl group, a difluoromethyl group, a fluoroethyl group, 1,1-difluoroethyl, 1,2-difluoroethyl, 1,1,2-trifluoroethyl, tetrafluoroethyl, chloromethyl, dichloromethyl, chloroethyl, 1,1-dichloroethyl, 1,2-dichloroethyl, 1,1,2-trichloroethyl, tetrachloroethyl, bromomethyl, dibromomethyl, bromoethyl, 1,1-dibromoethyl, 1,2-dibromoethyl, 1,1,2-tribromoethyl, tetrabromoethyl ethyl, 2-fluorophenyl, 3-fluorophenyl, 4-fluorophenyl, 2,3-difluorophenyl, 2,4-difluorophenyl, 2,5-difluorophenyl, 2,6-difluorophenyl, 2,3,4-trifluorophenyl, 2,3,5-trifluorophenyl, 2,3,6-trifluorophenyl, 2,3,4,5-tetrafluorophenyl, 2,3,4,6-tetrafluorophenyl, pentafluorophenyl, 2-chlorophenyl, 3-chlorophenyl, 4-chlorophenyl, 2,3-dichlorophenyl, 2,4-dichlorophenyl, 2,5-dichlorophenyl, 2,6-dichlorophenyl, 2,3,4-trichlorophenyl, 2,3,5-trichlorophenyl, 2,3,6-trichlorophenyl, 2,3,4,5-tetrachlorophenyl, 2,3,4,6-tetrachlorophenyl, pentachlorophenyl, 2-bromophenyl, 3-bromophenyl, 4-bromophenyl, 2,3-dibromophenyl, 2,4-dibromophenyl, 2,5-dibromophenyl, 2,6-dibromophenyl, 2,3,4-tribromophenyl, 2,3,5-tribromophenyl, 2,3,6-tribromophenyl, 2,3,4,5-tetrabromophenyl, 2,3,4,6-tetrabromophenyl, pentabromophenyl and the like.

Hydrocarbon groups having a substituent containing oxygen include methoxy, ethoxy, n-propoxy, isopropoxy, n-butoxy, sec-butoxy, tert-butoxy, isobutoxy, phenoxy, 2-methylphenoxy, 3-methylphenoxy, 4-methylphenoxy and the like, and halogen atoms include a fluorine atom, a chlorine atom, a bromine atom and an iodine atom.

Among these, each A and A' is preferably a phenylene group represented by the general formula(4). $R_5$ and $R_6$ include methyl, ethyl, n-propyl, isopropyl, n-butyl, sec-butyl, tert-butyl, phenyl, methoxy, ethoxy, a chlorine atom and a bromine atom, and as A and A', 1,2-phenylene, 1,2-(6-methylphenylene), 1,2-(6-tert-butylphenylene), 1,2-(4,6-dimethylphenylene), 1,2-(4,6-di-tert-butylphenylene), 1,2-(6-tert-butyl-4-methyl phenylene), 1,2-(6-tert-butyl-4-methoxy phenylene) and 1,2-(6-tert-butyl-4-bromophenylene) are more preferred.

E in the above-mentioned general formula(1) is the residual group of the element of the 13th to 15th Groups capable of bonding at three positions, and concrete examples of E include, for example, a nitrogen atom, a boron atom, a phosphorus atom, an alkylidyne group(formula(6)), a silanetolyl group(formula(7)) represented by the following general formula and the like, but are not restricted thereto.

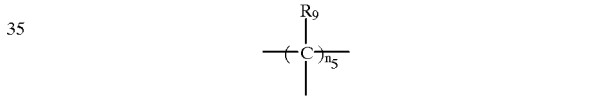

Each of $R_9$ and $R_{10}$ is a hydrogen atom or a hydrocarbon group or halogenated hydrocarbon group having 1 to 20 carbon atoms, and each of $n_5$ and $n_6$ is an integer of 1 to 20. Examples of $R_9$ and $R_{10}$ include methyl, ethyl, n-propyl, isopropyl, n-butyl, isobutyl, sec-butyl, tert-butyl, n-pentyl, neopentyl, n-hexyl, n-octyl, phenyl, 2-methylphenyl, 3-methylphenyl, 4-methylphenyl, 2,3-dimethylphenyl, 2,4-dimethylphenyl, 2,5-dimethylphenyl, 2,6-dimethylphenyl, 2,3,4-trimethylphenyl, 2,3,5-trimethylphenyl, 2,3,6-trimethylphenyl, 2,3,4,5-tetramethylphenyl, 2,3,4,6-tetramethylphenyl, pentamethylphenyl, fluoromethyl, difluoromethyl, fluoroethyl, 1,1-difluoroethyl, 1,2-difluoroethyl, 1,1,2-trifluoroethyl, tetrafluoroethyl, chloromethyl, dichloromethyl, chloroethyl, 1,1-dichloroethyl, 1,2-dichloroethyl, 1,1,2-trichloroethyl, tetrachloroethyl, bromomethyl, dibromomethyl, bromoethyl, 1,1-dibromoethyl, 1,2-dibromoethyl, 1,1,2-tribromoethyl, tetrabromoethyl, 2-fluorophenyl, 3-fluorophenyl, 4-fluorophenyl, 2,3-difluorophenyl, 2,4-difluorophenyl, 2,5-difluorophenyl, 2,6-difluorophenyl, 2,3,4-trifluorophenyl, 2,3,5-trifluorophenyl, 2,3,6-trifluorophenyl, 2,3,4,5-tetrafluorophenyl, 2,3,4,6-tetrafluorophenyl, pentafluorophenyl, 2-chlorophenyl, 3-chlorophenyl, 4-chlorophenyl, 2,3-dichlorophenyl, 2,4-dichlorophenyl, 2,5-dichlorophenyl, 2,6-dichlorophenyl, 2,3,4-trichlorophenyl, 2,3,5-trichlorophenyl, 2,3,6-trichlorophenyl, 2,3,4,5-tetrachlorophenyl, 2,3,4,6-tetrachlorophenyl, pentachlorophenyl, 2-bromophenyl, 3-bromophenyl, 4-bromophenyl, 2,3-dibromophenyl, 2,4-dibromophenyl, 2,5-dibromophenyl, 2,6-dibromophenyl, 2,3,4-tribromophenyl, 2,3,5-tribromophenyl, 2,3,6-tribromophenyl, 2,3,4,5-tetrabromophenyl, 2,3,4,6-tetrabromophenyl, pentabromophenyl and the like. Among these, a hydrogen atom, methyl, ethyl, n-propyl, isopropyl, n-butyl, sec-butyl, tert-butyl and phenyl are preferred.

Each of R and R' in the transition metal complex represented by the above-mentioned general formula (1) is a halogen atom or a hydrocarbon group having 1 to 20 carbon atoms. Examples of the halogen atom include, for example, fluorine atom, a chlorine atom, a bromine atom and an iodine atom, and examples of the hydrocarbon group having 1 to 20 carbon atoms include methyl, ethyl, n-propyl, isopropyl, n-butyl, phenyl, benzyl and the like. Among these, a chlorine atom, methyl and benzyl ate preferred.

R" in the transition metal complex represented by the above-mentioned general formula (1) is a hydrocarbon or halogenated hydrocarbon group containing at least one hetero atom and having 1 to 20 carbon atoms, and examples of the R" include a cyclic group containing a hetero atom, an alkoxy group, a (substituted)phenoxy group, a hydrocarbyl thio group, a hydrocarbyl amino group, a hydrocarbyl phosphino group or a hydrocarbon or halogenated hydrocarbon group having at least one of these group as a substituent.

The cyclic substituents containing a hetero atom include furyl, thienyl, benzothienyl, pyrrolyl, pyridyl, tetrahydrofuryl and tetrahydrothienyl, and thienyl or pyridyl is preferred.

The alkoxy groups include methoxy, ethoxy, propoxy, butoxy and the like, and methoxy or ethoxy is preferred.

The (substituted)phenoxy group in the present specification represents a non-substituted or substituted phenoxy group and examples include phenoxy, a methylphenoxy group, an ethylphenoxy group, a dimethylphenoxy group, a diethylphenoxy group and the like. Phenoxy and the methylphenoxy group are preferred.

The hydrocarbyl thio groups include methylthio, ethylthio, propylthio, butylthio, phenylthio and the like, and methylthio, ethylthio and phenylthio are preferred.

The hydrocarbyl amino groups include dimethylamino, diethylamino, dipropylamino, dibutylamino, diphenylamino and the like, and dimethylamino, diethylamino and diphenylamide are preferred.

The hydrocarbyl phosphino groups include dimethylphosphino, diethylphosphino, dipropylphosphino, dibutylphosphino, diphenyl phosphino and the like, and dimethylphosphino, diethylphosphino and diphenylphosphino are preferred.

The hydrocarbon group having a hetero atom-containing cyclic hydrocarbon group, an alkoxy group, a (substituted) phenoxy group, a hydrocarbyl thio group, a hydrocarbyl amino group or a hydrocarbyl phosphino group as a substituent include a furfuryl group, a thienyl group, methoxymethyl, ethoxymethyl, phenoxymethyl, methylthiomethy, ethylthiomethyl, phenylthiomethyl, dimethylaminomethyl group, diethylaminomethyl, diphenylaminomethyl, dimethylphosphinomethyl, diethylphosphinomethyl, diphenylphosphinomethyl and the like.

Concrete examples of the transition metal complex represented by the general formula (1) include, for example, 2,2'-(2-thienylmethylene)bisphenoxy titanium dichloride,
2,2'-(2-thienylmethylene)bis(6-methylphenoxy) titanium dichloride,
2,2'-(2-thienylmethylene)bis(6-tert-butylphenoxy) titanium dichloride,
2,2'-(2-thienylmethylene)bis(4,6-dimethylphenoxy) titanium dichloride,
2,2'-(2-thienylmethylene)bis(4,6-di-tert-butylphenoxy) titanium dichloride,
2,2'-(2-thienylmethylene)bis(6-tert-butyl-4-methylphenoxy) titanium dichloride,
2,2'-(2-thienylmethylene)bis(6-methyl-4-tert-butylphenoxy) titanium dichloride,
2,2'-(2-thienylmethylene)bis(3-tert-butyl-4,6-dimethylphenoxy) titanium dichloride,
2,2'-(2-thienylmethylene)bis(4,6-di-tert-butyl-3-methylphenoxy)titanium dichloride,
2,2'-(2-thienylmethylene)bis(6-tert-butyl-4-fluorophenoxy) titanium dichloride,
2,2'-(2-thienylmethylene)bis(6-tert-butyl-4-chlorophenoxy) titanium dichloride,
2,2'-(2-thienylmethylene)bis(6-tert-butyl-4-bromophenoxy) titanium dichloride,
2,2'-(2-thienylmethylene)bis(6-tert-butyl-4-methoxyphenoxy)titanium dichloride,
2,2'-(2-thienylmethylene)bis(6-tert-butyl-4-ethoxyphenoxy) titanium dichloride,
2,2'-(2-thienylmethylene)bis(6-tert-butyl-4-n-propoxyphenoxy)titanium dichloride,
2,2'-(2-thienylmethylene)bis(6-tert-butyl-4-isopropoxyphenoxy)titanium dichloride,
2,2'-(3-methyl-2-thienylmethylene)bis(6-tert-butyl-4-methylphenoxy)titanium dichloride,
2,2'-(4-methyl-2-thienylmethylene)bis(6-tert-butyl-4-methylphenoxy)titanium dichloride,
2,2'-(5-methyl-2-thienylmethylene)bis(6-tert-butyl-4-methylphenoxy)titanium dichloride,
2,2'-(3,4-dimethyl-2-thienylmethylene)bis(6-tert -butyl-4-methylphenoxy)titanium dichloride,
2,2'-(3,5-dimethyl-2-thienylmethylene)bis(6-tert-butyl-4-methylphenoxy)titanium dichloride,
2,2'-(3,4,5-trimethyl-2-thienylmethylene)bis(6-tert-butyl-4-methylphenoxy)titanium dichloride,
2,2'-(2,5-dimethyl-3-thienylmethylene)bis(6-tert-butyl-4-methylphenoxy)titanium dichloride,
2,2'-(2,4,5-trimethyl-3-thienylmethylene)bis(6-tert-butyl-4-methylphenoxy)titanium dichloride,
2,2'-(2-benzothienylmethylene)bis(6-tert-butyl-4-methylphenoxy) titanium dichloride,
2,2'-(2-furylmethylene)bis(phenoxy)titanium dichloride,
2,2'-(2-furylmethylene)bis(6-methylphenoxy)titanium dichloride, 2,2'-(2-furylmethylene)bis(6-tert-butylphenoxy)titanium dichloride,
2,2'-(2-furylmethylene)bis(4,6-dimethylphenoxy)titanium dichloride, 2,2'-(2-furylmethylene)bis(4,6 -di-tert-butylphenoxy)titanium dichloride,
2,2'-(2-furylmethylene)bis(6-tert-butyl-4-methylphenoxy) titanium dichloride,
2,2'-(2-furylmethylene)bis(6-methyl-4-tert-butylphenoxy) titanium dichloride,
2,2'-(2-furylmethylene)bis(3-tert-butyl-4,6-dimethylphenoxy)titanium dichloride,
2,2'-(2-furylmethylene)bis(6-tert-butyl-4-fluorophenoxy) titanium dichloride,
2,2'-(2-furylmethylene)bis(6-tert-butyl-4-chlorophenoxy) titanium dichloride,
2,2'-(2-furylmethylene)bis(6-tert-butyl-4-bromophenoxy) titanium dichloride, 2,2'-(2-furylmethylene)bis(6-tert-butyl-4-methoxyphenoxy) titanium dichloride,
2,2'-(2-furylmethylene)bis(6-tert-butyl-4-ethoxyphenoxy) titanium dichloride,
2,2'-(2-furylmethylene)bis(6-tert-butyl-4-n-propoxyphenoxy)titanium dichloride,
20 2,2'-(2-furylmethylene)bis(6-tert-butyl-4-isopropoxyphenoxy)titanium dichloride,
2,2'-(3-methyl-2-furylmethylene)bis(6-tert-butyl-4-methylphenoxy)titanium dichloride,
2,2'-(4-methyl-2-furylmethylene)bis(6-tert-butyl-4-methylphenoxy)titanium dichloride,
2,2'-(5-methyl-2-furylmethylene)bis(6-tert-butyl-4-methylphenoxy)titanium dichloride,
2,2'-(3,4-dimethyl-2-furylmethylene)bis(6-tert-butyl-4-methylphenoxy)titanium dichloride,
2,2'-(3,5-dimethyl-2-furylmethylene)bis(6-tert-butyl-4-methylphenoxy)titanium dichloride,
2,2'-(3,4,5-trimethyl-2-furylmethylene)bis(6-tert-butyl-4-methylphenoxy)titanium dichloride,
2,2'-(2,5-dimethyl-3-furylmethylene)bis(6-tert-butyl-4-methylphenoxy)titanium dichloride,
2,2'-(2,4,5-trimethyl-3-furylmethylene)bis(6-tert-butyl-4-methylphenoxy)titanium dichloride,
2,2'-(2-benzofurylmethylene)bis(6-tert-butyl-4-methylphenoxy)titanium dichloride,
2,2'-(2-pyridylmethylene)bis(phenoxy)titanium dichloride,
2,2'-(2-pyridylmethylene)bis(6-methylphenoxy)titanium dichloride, 2,2'-(2-pyridylmethylene)bis(6-tert-butylphenoxy) titanium dichloride,
2,2'-(2-pyridylmethylene)bis(4,6-dimethylphenoxy) titanium dichloride, 2,2'-(2-pyridylmethylene)bis(4,6-di-tert-butylphenoxy) titanium dichloride,
2,2'-(2-pyridylmethylene)bis(6-tert-methylphenoxy) titanium dichloride, 2,2'-(2-pyridylmethylene)bis(6-methyl-4-tert-butylphenoxy)titanium dichloride,
2,2'-(2-pyridylmethylene)bis(3-tert-butyl-4,6-dimethylphenoxy)titanium dichloride,
2,2'-(2-pyridylmethylene)bis(6-tert-butyl-4-fluorophenoxy) titanium dichloride,
2,2'-(2-pyridylmethylene)bis(6-tert-butyl-4-chlorophenoxy) titanium dichloride,
2,2'-(2-pyridylmethylene)bis(6-tert-butyl-4-bromophenoxy) titanium dichloride,
2,2'-(2-pyridylmethylene)bis(6-tert-butyl-4-methoxyphenoxy)titanium dichloride,
2,2'-(2-pyridylmethylene)bis(6-tert-butyl-4-ethoxyphenoxy)titanium dichloride,
2,2'-(2-pyridylmethylene)bis(6-tert-butyl-4-n-propoxyphenoxy)titanium dichloride,
2,2'-(2-pyridylmethylene)bis(6-tert-butyl-4-isopropoxyphenoxy)titanium dichloride,
2,2'-(3-methyl-2-pyridyl methylene)bis(6-tert-butyl-4-methylphenoxy)titanium dichloride,
2,2'-(4-methyl-2-pyridylmethylene)bis(6-tert-butyl-4-methylphenoxy)titanium dichloride,
2,2'-(5-methyl-2-pyridylmethylene)bis(6-tert-butyl-4-methylphenoxy)titanium dichloride,
2,2'-(3,4-dimethyl-2-pyridylmethylene)bis(6-tert-butyl-4-methylphenoxy)titanium dichloride,
2,2'-(3,5-dimethyl-2-pyridylmethylene)bis(6-tert-butyl-4-methylphenoxy)titanium dichloride,
2,2'-(3,4,5-trimethyl-2-pyridylmethylene)bis(6-tert-butyl-4-methylphenoxy)titanium dichloride,
2,2'-(3-pyridyl methylene)bis(6-tert-butyl-4-methylphenoxy)titanium dichloride,
2,2'-(2-methyl-3-pyridylmethylene)bis(6-tert-butyl-4-methylphenoxy)titanium dichloride,
2,2'-(4-methyl-3-pyridylmethylene)bis(6-tert-butyl-4-methylphenoxy)titanium dichloride,
2,2'-(5-methyl-3-pyridylmethylene)bis(6-tert-butyl-4-methylphenoxy)titanium dichloride,
2,2'-(2,4-dimethyl-3-pyridylmethylene)bis(6-tert-butyl-4-methylphenoxy)titanium dichloride,
2,2'-(2,5-dimethyl-3-pyridylmethylene)bis(6-tert-butyl-4-methylphenoxy)titanium dichloride,
2,2'-(2,4,5-trimethyl-3-pyridylmethylene)bis(6-tert-butyl-4-methylphenoxy)titanium dichloride,
2,2'-(2-quinolylmethylene)bis(6-tert-butyl-4-methylphenoxy)titanium dichloride,
2,2'-(3-quinolylmethylene)bis(6-tert-butyl-4-methylphenoxy)titanium dichloride,
2,2'-(2-thienylmethylene)bis(naphthyloxy)titanium dichloride, 2,2'-(3-thienylmethylene)bis(naphthyloxy) titanium dichloride,
2,2'-(5-methyl-2-thienylmethylene)bis(naphthyloxy) titanium dichloride,
2,2'-(5-methyl-3-thienylmethylene)bis(naphthyloxy) titanium dichloride,
2,2'-(2,5-dimethyl-3-thienylmethylene)bis(naphthyloxy) titanium dichloride,
2,2'-(2-benzothienylmethylene)bis(naphthyloxy)titanium dichloride, 2,2'-(2-benzothienylmethylene)bis(naphthyloxy) titanium dichloride,
2,2'-(3-benzothienylmethylene)bis(naphthyloxy)titanium dichloride,
2,2'-(2-thienylmethylene)bis(8-methylnaphthyloxy)titanium dichloride,
2,2'-(2-thienylmethylene)bis(8-tert-butylnaphthyloxy) titanium dichloride,
2,2'-(2-thienylmethylene)bis(4,8-dimethylnaphthyloxy) titanium dichloride,
2,2'-(2-thienylmethylene)bis(8-tert-butyl-4-methylnaphthyloxy) titanium dichloride,
2,2-(2-furylmethylene)bis(naphthyloxy)titanium dichloride,
2,2'-(3-furylmethylene)bis(naphthyloxy)titanium dichloride,
2,2'-(5-methyl-2-furylmethylene)bis(naphthyloxy )titanium dichloride, 2,2'-(5-methyl-3-furylmethylene)bis (naphthyloxy) titanium dichloride, 2,2'-(2,5-dimethyl-3-furylmethylene) bis(naphthyloxy)titanium dichloride, 2,2'-(2-benzofurylmethylene)bis(naphthyloxy)titanium dichloride,
2,2'-(3-benzofurylmethylene)bis(naphthyloxy)titanium dichloride, 2,2'-(2-furylmethylene)bis(8-methylnaphthyloxy) titanium dichloride, 2,2'-(2-furylmethylene)bis(8-tert-butylnaphthyloxy)titanium dichloride,
2,2'-(2-furylmethylene)bis(4,8-dimethylnaphthyloxy) titanium dichloride, 2,2'-(2-furylmethylene)bis(8-tert-butyl-4-methylnaphthyloxy)titanium dichloride,
2,2'-(2-pyridylmethylene)bis(naphthyloxy)titanium dichloride, 2,2'-(3-pyridylmethylene)bis(naphthyloxy) titanium dichloride, 2,2'-(5-methyl-2-pyridylmethylene) bis (naphthyloxy)titanium dichloride, 2,2'-(5-methyl-3-pyridylmethylene)bis(naphthyloxy)titanium dichloride,
2,2'-(2,5-dimethyl-3-pyridylmethylene)bis(naphthyloxy) titanium dichloride,
2,2'-(2-quinolylmethylene)bis(naphthyloxy)titanium dichloride, 2,2'-(3-quinolylmethylene)bis(naphthyloxy) titanium dichloride, 2,2'-(2-pyridylmethylene)bis(8-methylnaphthyloxy)titanium dichloride,
2,2'-(2-pyridylmethylene)bis(8-tert-butylnaphthyloxy) titanium dichloride, 2,2'-(2-pyridylmethylene)bis(4,8-dimethylnaphthyloxy)titanium-dichloride, 2,2'-(2-pyridylmethylene)bis(8-tert-butyl-4-methylnaphthyloxy)titanium dichloride,
3-(2-thienyl)-1,5-pentamethylenedioxytitanium dichloride,
3-(3-thienyl)-1,5-pentamethylenedioxytitanium dichloride,
3-(2-benzothienyl)-1,5-pentamethylenedioxytitanium dichloride, 1,5-dimethyl-3-(2-thienyl)-1,5-pentamethylenedioxytitanium dichloride, 1,5-di-tert-butyl-3-(2-thienyl)-1,5-pentamethylenedioxytitanium dichloride,
1,2,4,5-tetramethyl-3-(2-thienyl)-1,5-pentamethylenedioxytitanium dichloride,
1,5-di-tert-butyl-2,4-dimethyl-3-(2-thienyl)-1,5-pentamethylenedioxytitanium dichloride,
3-(2-furyl)-1,5-pentamethylenedioxytitanium dichloride,
3-(3-furyl)-1,5-pentamethylenedioxytitanium dichloride,
3-(2-benzofuryl)-1,5-pentamethylenedioxytitanium dichloride,
3-(2-furyl)-1,5-dimethyl-1,5-pentamethylenedioxytitanium dichloride, 1,5-di-tert-butyl-3-(2-furyl)-1,5-pentamethylenedioxytitanium dichloride,
3-(2-furyl)-1,2,4,5-tetramethyl-1,5-pentamethylenedioxytitanium dichloride,
3-(2-pyrrolyl)-1,5-pentamethylenedioxytitanium dichloride,
3-(3-pyrrolyl)-1,5-pentamethylenedioxytitanium dichloride,
3-(2-indolyl)-1,5-pentamethylenedioxytitanium dichloride,
3-(2-pyrrolyl)-1,5-dimethyl-1,5-pentamethylenedioxytitanium dichloride, 1,5-di-tert-butyl-3-(2-pyrrolyl)-1,5-pentamethylenedioxytitanium dichloride,
1,2,4,5-tetramethyl-3-(2-pyrrolyl)-1,5-pentamethylenedioxytitanium dichloride,
1,5-di-tert-butyl-1,5-dimethyl-3-(2-pyrrolyl)-pentamethylenedioxytitanium dichloride,
3-(2-pyridyl)-1,5-pentamethylenedioxytitanium dichloride,
3-(3-pyridyl)-1,5-pentamethylenedioxytitanium dichloride,
3-(2-quinolyl)-1,5-pentamethylenedioxytitanium dichloride,
3-(2-pyridyl)-1,5-dimethyl-1,5-pentamethylenedioxytitanium dichloride, 1,5-di-tert-butyl-3-(2-pyridyl)-1,5-pentamethylenedioxytitanium dichloride,
1,2,4,5-tetramethyl-3-(2-pyridyl)-1,5-pentamethylenedioxytitanium dichloride,
1,5-di-tert-butyl-1,5-dimethyl-3-(2-pyridyl)-1,5-pentamethylenedioxytitanium dichloride and the like.

The transition metal complex can be synthesized for example, by the following methods. There are illustrated a method for obtaining the transition metal complex comprising treating a phenol compound with a Grignard reagent under an inert atmosphere, reacting the treated matter with an aldehyde or ketone compound in an amount of half equivalent to the phenol compound used in the treatment to obtain a bisphenol derivative and then reacting a transition metal compound with the bisphenol derivative, a method for obtaining the transition metal complex comprising treating a phenol compound of which hydroxy group is protected with a proper functional group with an alkyl lithium under an inert atmosphere, reacting the treated matter with a dihalogenated phosphorus compound in an amount of half equivalent to the phenol compound used in the treatment to obtain a bisphenol derivative, and after treating the the bisphenol derivative with a Grignard reagent, reacting thus treated matter with a a transition metal compound, and the like.

The compounds (A) used in the present invention are either of (A1): the organoaluminum compound represented by the general formula; $R^1{}_aAlZ_{3-a}$, (A2): the cyclic aluminoxane having a structure represented by the general formula; $\{-Al(R^2)-O-\}_b$, (A3): the linear aluminoxane having a structure represented by the general formula; $R^3(R^3-Al-O)_cAlR^3{}_2$ (wherein each of $R^1$, $R^2$ and $R^3$ is a hydrocarbon group having 1 to 8 carbon atoms, and all of $R^1$, all of $R^2$ and all of $R^3$ may be the same or different. Z represents a hydrogen atom or a halogen atom and may contain 2 or more kinds of Zs in the molecule. a is a number satisfying $0<a\leq 3$, b represents an integer of 2 or more and c represents an integer of 1 or more.) or a mixture of at least two of those.

The examples of (A1) of the organoaluminum compound represented by the general formula; $R^1{}_aAlZ_{3-a}$ include trialkylaluminums such as trimethylaluminum, triethylaluminum, tripropylaluminum, triisobutylaluminum, trihexylaluminum and the like; dialkylaluminum chlorides such as dimethylaluminum chloride, diethylaluminum chloride, dipropylaluminum chloride, diisobutylaluminum chloride, dihexylaluminum chloride and the like; alkylaluminum sesquichlorides such as methylaluminum sesquichloride, ethylaluminum sesquichloride and the like; alkylaluminum dichlorides such as methylaluminum dichloride, ethylaluminum dichloride, propylaluminum dichloride, isobutylaluminum dichloride, hexyl aluminum dichloride and the like; dialkylaluminum hydrides such as dimethylaluminum hydride, diethylaluminum hydride, dipropylaluminum hydride, diisobutylaluminum hydride, dihexylaluminum hydride and the like, etc. Trialkylaluminums are preferred, and triethylaluminum and triisobutylaluminum are more preferred.

Each of $R^2$ and $R^3$ in (A2) of the cyclic aluminoxane having a structure represented by the general formula; $\{-Al(R^2)-O-\}_b$, and (A3) of the linear aluminoxane having a structure represented by the general formula; $R^3(R^3-Al-O)_cAlR^3{}_2$ is a hydrocarbon group having 1 to 8 carbon atoms, and as the concrete examples, alkyl groups such as methyl, ethyl, n-propyl, isopropyl, n-butyl, isobutyl, n-pentyl, neopenyl and the like can be exemplified. b is an integer of 2 or more and c is an integer of 1 or more. Preferably each of $R^2$ and $R^3$ is methyl and isobutyl, b is 2 to 40, and c is 1 to 40.

The above-mentioned aluminoxanes can be prepared by various methods. The procedure is not particularly restricted, and they may be prepared according to well-known methods. For example, they are prepared by contacting a solution dissolving a trialkylaluminum (for example, trimethylaluminum or the like) in a suitable organic solvent (benzene, an aliphatic hydrocarbon or the like) with water. As another method, there is mentioned a method for preparing the aluminoxanes by contacting trialkylaluminum (for example, trimethylaluminum or the like) with a metal salt containing crystal water (for example, a hydrate of cupric sulfate or the like).

As a compound(B) in the present invention, a boron compound(B1) represented by the general formula $BQ^1Q^2Q^3$, a boron compound(B2) represented by the general formula $Z^+(BQ^1Q^2Q^3Q^4)^-$, or a boron compound(B3) represented by the general formula $(L-H)^{30} BQ^1Q^2Q^3Q^4)^-$.

In the boron compound(B1) represented by the general formula $BQ^1Q^2Q^3$, B is a tri-valent boron, each of $Q^1$, $Q^2$ and $Q^3$ is a halogen atom, a hydrocarbon group having 1 to 20 carbon atoms, a halogenated hydrocarbon group having 1 to 20 carbon atoms, a silyl group having 1 to 20 carbon atoms, an alkoxy group having 1 to 20 carbon atoms, or an amide group having 1 to 20 carbon atoms, and they may be the same or different.

The examples of the Lewis acid (B1) include tris(pentafluorophenyl)borane, tris(2,3,5,6-tetrafluorophenyl)

borane, tris(2,3,4,5-tetrafluorophenyl)borane, tris(3,4,5-trifluorophenyl)borane, tris(2,3,4-trifluorophenyl)borane, phenylbis(pentafluorophenyl)borane and the like. Tris(pentafluorophenyl)borane is most preferred.

In the boron compound(B2) represented by the general formula $Z^+(BQ^1Q^2Q^3Q^4)^-$, B is boron having a tri-valent valence state, each definition of $Q^1$ to $Q^4$ is the same as that of $Q^1$ in the boron compound(B1).

As the examples of the compounds(B2) represented by the general formula $Z^+(BQ^1Q^2Q^3Q^4)^-$, $Z^+$ being an inorganic cation includes a ferrocenium cation, an alkyl substituted ferrocenium cation, a silver cation, etc., and $Z^+$ being an organic cation capable of extracting a ligand from the transition metal compound formed in the reaction of the transition metal compound represented by the above-mentioned general formula (1) with the compound (A) includes a triphenylmethyl cation and the like. The $(BQ^1Q^2Q^3Q^4)^-$ includes tetrakis(pentafluorophenyl)borate, tetrakis(2,3,5,6-tetrafluorophenyl)borate, tetrakis(2,3,4,5-tetrafluorophenyl)borate, tetrakis(3,4,5-trifluorophenyl)borate, tetrakis(2,2,4-trifluorophenyl)borate, phenylbis(pentafluorophenyl)borate, tetrakis[3,5-bis(trifluoromethylphenyl)]borate and the like. These concrete combinations include ferrocenium tetrakis(pentafluorophenyl)borate, 1,1'-dimethylferrocenium tetrakis(pentafluorophenyl)borate, silver tetrakis(pentafluorophenyl)borate, triphenylmethyl tetrakis(pentafluorophenyl)borate, triphenylmethyl tetrakis[3,5-bis(trifluoromethylphenyl)]borate and the like, and triphenylmethyl tetrakis(pentafluorophenyl)borate is most preferred.

In the boron compound (B3) represented by the above-mentioned general formula $(L-H)^+(BQ^1Q^2Q^3Q^4)^-$, L is a neutral Lewis base, $(L-H)^+$ is a Brônsted acid and each definition of $Q^1$ to $Q^4$ is the same as that of $Q^1$ in the above-mentioned boron compound(B1). As the examples of the compound represented by the general formula $(L-H)^+(BQ^1Q^2Q^3Q^4)^-$, $(L-H)^+$ being a Brônsted acid includes a substituted trialkylammonium, a N,N-dialkylanilinium, a dialkylammonium, a triarylphosphonium and the like, and $(BQ^1Q^2Q^3Q^4)^-$ includes the same anions described above. The examples of these combinations include triethylammonium tetrakis(pentafluorophenyl)borate, tripropylammonium tetrakis(pentafluorophenyl)borate, tri(n-butyl) ammonium tetrakis(pentafluorophenyl)borate, tri (n-butyl) ammonium tetrakis[3,5-bis(trifluoromethylphenyl)]borate, N,N-dimethylanilinium tetrakis(pentafluorophenyl)borate, N,N-diethylanilinium tetrakis(pentafluorophenyl)borate, N,N-2,4,6-pentamethylanilinium tetrakis(pentafluorophenyl) borate, N,N-dimethylanilinium tetrakis[3,5-bis(trifluoromethylphenyl)] borate, diisopropylammonium tetrakis(pentafluorophenyl)borate, dicyclohexylammonium tetrakis(pentafluorophenyl)borate, triphenylphosphonium tetrakis(pentafluorophenyl)borate, tri(methylphenyl)phosphonium tetrakis(pentafluorophenyl) borate, tri(dimethylphenyl)phosphonium tetrakis(pentafluorophenyl) borate and the like. Tri(n-butyl) ammonium tetrakis(pentafluorophenyl)borate or N,N-dimethylanilinium tetrakis(pentafluorophenyl)borate is most preferred.

In the present invention, the transition metal complex represented by the general formula (1) and the compound (A) or the transition metal complex, the compound (A) and the compound (B) may be fed into a polymerization vessel with an arbitrary order and be used. Moreover, the reaction product obtained by contacting the transition metal complex represented by the general formula (1) and the compound (A) or the transition metal complex, the compound (A) and the compound (B) in any combinations thereof in advance may be used.

Concerning the amount of each catalyst component used, it is desirable to use each component in the molar ratio of the compound (A)/the transition metal complex of 0.1 to 10000 and preferably 5 to 2000, and the molar ratio of the compound (B)/the transition metal of 0.01 to 100 and preferably 0.5 to 10. Concerning the concentration of each catalyst component used in a solution state, it is desirable to use the transition metal complex represented by the general formula (1) at the concentration of 0.0001 to 5 mmol/l and preferably 0.001 to 1 mmol/l, the compound (A) in terms of Al atom, at the concentration of 0.01 to 500 mmol/l and preferably 0.1 to 100 mmol/l, and the compound (B) at the concentration of 0.0001 to 5 mmol/l and preferably 0.001 to 1 mmol/l.

In the present invention, as the monomer constituting the olefin polymer, any of olefins and diolefins having 2 to 20 carbon atoms and the like can be used and at the same time two kinds or more of the monomers can be used. The concrete examples include ethylene, propylene, butene-1, pentene-1, hexene-1, heptene-1, octene-1, nonene-1, decene-1,4-methylpentene-1, vinyl cyclohexene and the like. However, the present invention should not be limited to the above-mentioned compounds. The concrete examples of the monomers constituting a copolymer include ethylene/propylene, ethylene/butene-1, ethylene/hexene-1, propylene/butene-1 and the like. However, the present invention should not be limited to the above-mentioned compounds.

The polymerization method should not particularly be limited. For example, a solvent polymerization or slurry polymerization using an aliphatic hydrocarbon such as butane, pentane, hexane, heptane, octane or the like, an aromatic hydrocarbon such as benzene, toluene or the like, or a halogenated hydrocarbon such as methylenedichloride or the like as a solvent, a vapor phase polymerization in the gaseous monomer or the like is possible and either of a continuous polymerization and a batchwise polymerization is possible.

A polymerization temperature can be in the range of $-50°$ C. to $200°$ C., in particular, the range of $-20°$ C. to $100°$ C. is preferred, and a polymerization pressure is preferably in the range of from an atmospheric pressure to 60 kg/cm$^2$. A polymerization time is usually determined appropriately according to the kind of a polymer aimed and a reaction apparatus, and a range of 5 minutes to 20 hours can be adopted. A chain transfer agent such as hydrogen or the like can be added in order to control the molecular weight of the copolymer to be obtained.

EXAMPLE

The present invention is illustrated in detail according to Examples and Comparative Examples as follows, but the present invention is not restricted thereto.

The properties of the polymers in Examples were measured by the following methods.

(1) An intrinsic viscosity [η] was measured with an Ubbelohde type viscometer at 130° C. in tetralin solution. Generally, the higher is the molecular weight, the higher is the viscosity of the solution and the lager is the value of [η].

(2) An α-olefin content was determined according to the characteristic absorptions of ethylene and an α-olefin by using an infrared spectrophotometer (IR-810 manufactured by Nippon Bunkou Industry Ltd.) and expressed as the number of short branched-chains per 1000 carbon atoms(SCB).

(3) A melting point of the copolymer was determined under the following condition by DSC (SSC-5200 manufactured by Seikoh Ltd.). Raise of temperature: 40° C.–150° C. (10° C./min.), retaining for 5 minutes. Cooling: 150° C.–10° C. (5° C./min.), retaining for 10 minutes. Measurement: 10° C.–160° C. (5° C./min.)

(4) A molecular weight and a molecular weight distribution were determined with gel permeation chromatograph (150, C manufactured by Waters Company Ltd.) under the following conditions.

Column: TSK gel GMH-HT

Measurement temperature: set at 145° C.

Measurement concentration: 10 mg/10 ml-ODCB

Example 1

(1) Synthesis of 2-bis(2-hydroxy-3-tert-butyl-5-methylphenyl)methylthiophene

In an atmosphere of nitrogen, 16.42 g(100 mmol) of 2-tert-butyl-4-methylphenol was dissolved in 100 ml of diethyl ether and 33.3 ml of methylmagnesium bromide (100 mmol of diethyl ether solution) was added dropwise to this at 0° C. taking 5 minutes. After completion of the dropwise addition, the mixture was stirred at 25° C. for 10 minutes. After that, the diethyl ether was evaporated under vacuum, and 150 ml of toluene was added to obtain a toluene solution of 2-tert-butyl-4-methylphenoxymagnesium bromide. To the solution, 5.61 g (50 mmol) of 2-thiophenecarboxyaldehyde wag added dropwise at 25° C. After stirring for 24 hours, 5% aqueous hydrochloric acid solution was added and aqueous layer was separated. After the organic layer was washed with a saturated aqueous sodium chloride solution, it was dried with anhydrous magnesium sulfate and the solvent was removed by evaporation. The residue was purified by a silicagel column chromatography (a developing solvent: hexane/ethyl acetate=30/1) to obtain 2-bis(2-hydroxy-3-tert-butyl-5-methylphenyl) methylthiophene in a yield of 63%.

The $^1$H-NMR spectrum data of the compound is shown below. δ1.37(18H), 2.20(6H), 4.94(2H), 5.85(1H), 6.67 (2H), 6.83(1H), 6.97(1H), 7.05(1H), 7.26(1H)

(2) Synthesis of 2,2'-(2-thienylmethylene)bis(6-tert-butyl-4-methylphenoxy)titanium dichloride In an atmosphere of argon, 0.423 g (1.0 mmol) of 2-bis (2-hydroxy-3-tert-butyl-5-methylphenyl)methylthiophene synthesized in (1) and 10 ml of toluene were charged in a 50 ml Schlenk tube equipped with a stirrer, and the solution was kept at 20° C. To the solution, 0.11 ml (1.0 mmol) of titanium tetrachloride was slowly added with a syringe. The solution was continuously stirred for 12 hours. After stirring, the wine red solution obtained was concentrated, and the residue was washed with hexane to obtain orange crystals by filtration. After that, it was dried under vacuum to obtain 0.339 g of an orange solid material.

The $^1$H-NMR ($C_6D_6$) data of the solid material is shown below. δ1.45 (18H), 2.05 (6H), 6.38 (1H), 6.81 (1H), 6.83 (1H), 6.95 (2H), 7.55 (2H) According to the data, the orange solid material was identified as 2,2'-(2-thienylmethylene)bis (6-tert-butyl-4-methylphenoxy)titanium dichloride represented by the formula below:

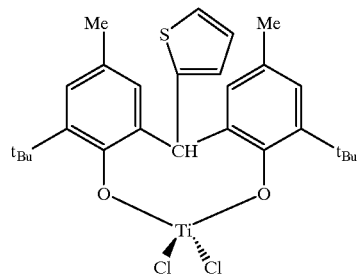

(3) Polymerization

After an autoclave reactor having an inner volume of 400 ml and a stirrer had been dried under vacuum and its atmosphere was substituted with argon, 170 ml of toluene as a solvent and 30 ml of hexene-1 as an α-olefin were charged and the temperature of the reactor was raised to 80° C. After the raise of the temperature, ethylene was fed while regulating an ethylene pressure at 6 kg/cm$^2$ and after the inner system was stabilized, 0.25 mmol of triethylaluminum was charged, and successively, 5.0 μmol of 2,2'-(2-thienylmethylene)bis(6-tert-butyl-4-methylphenoxy)titanium dichloride was charged. Successively, 15 μmol of triphenylmethyl tetrakis(pentafluorophenyl)borate was charged. While regulating the temperature at 80° C., the polymerization was carried out for 10 minutes. As a result of the polymerization, 1.7×10$^6$ g of an ethylene-hexene-1 copolymer having SCB of 19.8, [η] of 1.61, a molecular weight(Mw) of 1.7×10$^5$, a molecular weight distribution(Mw/Mn) of 2.6 and a melting point of 107.4° C. was produced per 1 mol of titanium.

Comparative Example (1) Polymerization

After an autoclave having an inner volume of 400 ml and a stirrer was dried under vacuum and its atmosphere was replaced with argon, 170 ml of toluene as a solvent and 30 ml of hexene-1 as an α-olefin were charged and the temperature of the reactor was raised to 80° C. After the raise of the temperature, ethylene was fed while regulating an ethylene pressure at 6 kg/cm$^2$ and after the inner system was stabilized, 0.25 mmol of triethylaluminum was charged, and successively, 5.0 μmol of 2,2'-thiobis(6-tert-butyl-4-methylphenoxy)titanium dichloride represented by the formula below was charged.

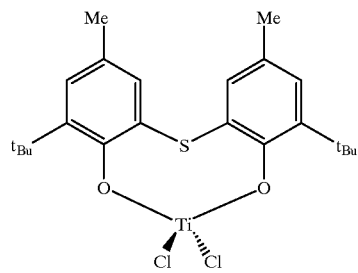

Successively, 15.0 μmol of triphenylmethyl tetrakis (pentafluorophenyl)borate was charged. While regulating the temperature at 80° C., the polymerization was carried out for 60 minutes. As a result of the polymerization, 2.9×10$^4$ g of an ethylene-hexene-1 copolymer having a SCB of 26.1, a [η] of 3.78 and a melting point of 116.8° C. was produced per 1 mol of titanium.

Example 2

(1) Synthesis of 2-bis(2-hydroxy-3-tert-butyl-5-methylphenyl)methylpyridine

In an atmosphere of nitrogen, 3.29 g(20 mmol) of 2-tert-butyl-4-methylphenol was dissolved in 10 ml of diethyl ether and 6.7 ml of methylmagnesium bromide (20 mmol of diethyl ether solution) was added dropwise to this at 0° C. for 5 minutes.

After completion of the dropwise addition, the reaction mixture was stirred at 25° C. for 10 minutes, subsequently, the diethyl ether was evaporated under vacuum, and 30 ml of toluene was added to obtain a toluene solution of 2-tert-butyl-4-methylphenoxymagnesium bromide. To the solution, 1.07 g (10 mmol) of picolinaldehyde was added dropwise at 25° C. and it was reacted for 5 hours while refluxing. After cooling, the reaction was stopped by adding aqueous 5% hydrochloric acid solution and successively, after neutralizing it with aqueous-sodium hydrogencarbonate solution, the organic layer obtained was washed with a saturated aqueous sodium chloride solution. After drying it over anhydrous magnesium sulfate, the solvent was distilled off. The residue was purified by a silicagel column chromatography (a developing solvent: hexane/ethyl acetate=20/1–1/1) to obtain 2-bis(2-hydroxy-3-tert-butyl-5-methylphenyl)methylpyridine.

The $^1$H-NMR spectrum data of the compound is shown below. δ1.33(18H), 2.20(16H), 5.32(1H), 6.73(2H), 7.00 (2H), 7.25(1H), 7.41(1H), 7.61(1H), 8.36(1H)

(2) Synthesis of 2,2'-(2-pyridylmethylene)bis(6-tert-butyl-4-methylphenoxy)titanium dichloride Under an atmosphere of argon, 0.209 g (0.5 mmol) of 2-bis(2-hydroxy-3-tert-butyl-5-methylphenyl)methylpyridine synthesized in (1) and 5.0 ml of toluene were charged in a 50 ml Schlenk tube equipped with a stirrer, and the solution was kept at 20° C. 0.055 ml (0.5 mmol) of titanium tetrachloride was slowly added to the solution with a syringe. The solution was continuously stirred for 12 hours. After stirring, a dark brown solid material was precipitated. The dark brown solid material was filtered and washed with hexane. Successively, it was dried under vacuum to obtain 0.077 g of 2,2'-(2-pyridylmethylene)bis(6-tert-butyl-4-methylphenoxy)titanium dichloride as a dark brown solid material represented by the formula below.

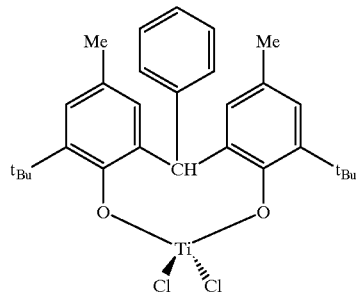

(3) Polymerization

After an autoclave having an inner volume of 400 ml and a stirrer was dried under vacuum and its atmosphere was replaced with argon, 170 ml of toluene as a solvent and 30 ml of hexene-1 as an α-olefin were charged and the temperature of the reactor was raised to 80° C. After the raise of the temperature, ethylene was fed while regulating an ethylene pressure at 6 kg/cm$^2$ and after the inner system was stabilized, 0.25 mmol of triethylaluminum was charged, and then, 5.0 μmol of 2,2'-(2-pyridylmethylene)bis(6-tert-butyl-4-methylphenoxy)titanium dichloride was charged.

Successively, 15 μmol of triphenylmethyl tetrakis (pentafluorophenyl)borate was charged. While regulating the temperature at 80° C., the polymerization was carried out for 30 minutes.

As a result of the polymerization, 4.7×10$^5$ g of an ethylene-hexene-1 copolymer having SCB of 19.20, [η] of 1.26, a molecular weight(Mw) of 1.1×10$^5$ and a molecular weight distribution(Mw/Mn) of 8.8 was produced per 1 mol of titanium and an hour.

Example 3

(1) Synthesis of 2-bis(2-hydroxy-3,5-di-tert-butyl-6-methylphenyl)thiophene

It was synthesized in the same manner as in Example 1 (1) except the use of 2,4-di-tert-butyl-5-methylphenol in place of 2-tert-butyl-4-methylphenol.

(2) Synthesis of 2,2'-(2-thienylmethylene)bis(4,6-di-tert-butyl-3-methylphenoxy)titanium dichloride Under an atmosphere of argon, 0.534 g (1.0 mmol) of 2-bis(2-hydroxy-3,5-di-tert-butyl-6-methylphenyl) and 10 ml of hexane were charged in a 50 ml Schlenk tube equipped with a stirrer, and the solution was kept at 20° C. To the solution, 0.11 ml (1.0 mmol) of titanium tetrachloride was slowly added with a syringe. The solution was continuously stirred for 12 hours. After stirring, a dark brown solid material was precipitated. The dark brown solid material was filtered and washed with hexane. Successively, it was dried under vacuum to obtain 0.3 g of 2,2'-(2-thienylmethylene)bis(4,6-di-tert-butyl-3-methylphenoxy) titanium dichloride as a dark brown solid material represented by the formula below.

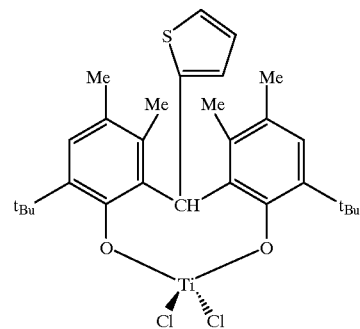

(3) Polymerization

After an autoclave having an inner volume of 400 ml and a stirrer was dried under vacuum and its atmosphere was replaced with argon, 170 ml of toluene as a solvent and 30 ml of hexene-1 as an α-olefin were charged and the temperature of the reactor was raised to 80° C. After the raise of the temperature, ethylene was fed while regulating an ethylene pressure at 6 kg/cm$^2$ and after the inner system was stabilized, 0.25 mmol of triethylaluminum was added, and successively, 5.0 μmol of 2,2'-(2-thienylmethylene)bis(4,6-di-tert-butyl-3-methylphenoxy)titanium dichloride was added. Successively, 15 μmol of triphenylmethyl tetrakis (pentafluorophenyl)borate was added. While regulating the temperature at 80° C., the polymerization was carried out for 60 minutes.

As a result of the polymerization, 2.4×10$^5$ g of an ethylene-hexene-1 copolymer having SCB of 34.64, [η] of 3.23, a molecular weight(Mw) of 3.0×10$^5$ and a molecular weight distribution(Mw/Mn) of 13.8 was produced per 1 mol of titanium.

Example 4

(1) Synthesis of 2-bis(2-hydroxy-3-tert-butyl-5-methylphenyl)methyl-5-methylthiophene It was synthesized in the same manner as in Example 1 (1) except the use of 5-methyl-2-thiophenecarboxyaldehyde in place of thiophenecarboxyaldehyde.

(2) Synthesis of 2,2'-(5-methyl-2-thienylmethylene)bis(6-tert-butyl-4-methylphenoxy)titanium dichloride Under an atmosphere of argon, 0.837 g (2.0 mmol) of 2-bis(2-hydroxy-3-tert-butyl-5-methylphenyl)methyl-4-methylthiophene and 20 ml of toluene were charged in a 50 ml Schlenk tube equipped with a stirrer, and the solution was kept at 20° C. To the solution, 0.22 ml (2.0 mmol) of titanium tetrachloride was slowly added with a syringe. The solution was continuously stirred for 12 hours. After stirring, a pale orange solid material was precipitated. The pale orange solid material was filtered and washed with hexane. Successively, it was dried under vacuum to obtain 0.2 g of 2,2'-(5-methyl-2-thienylmethylene)bis(6-di-tert-butyl-4-methylphenoxy)titanium dichloride as a pale orange solid material represented by the formula below.

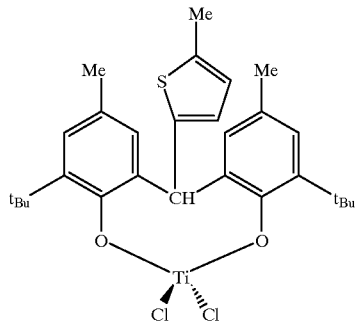

(3) Polymerization

After an autoclave having an inner volume of 400 ml and a stirrer was dried under vacuum and its atmosphere was replaced with argon, 170 ml of toluene as a solvent and 30 ml of hexene-1 as an α-olefin were charged and the temperature of the reactor was raised to 80° C. After the raise of the temperature, ethylene was fed while regulating an ethylene pressure at 6 kg/cm$^2$ and after the inner system was stabilized, 0.25 mmol of triethylaluminum was added, and successively, 5.0 μmol of 2,2'-(5-methyl-2-thienylmethylene)bis(6-tert-butyl-4-methylphenoxy) titanium dichloride was added. Successively, 15 μmol of triphenylmethyl tetrakis(pentafluorophenyl)borate was charged. While regulating the temperature at 80° C., the polymerization was carried out for 60 minutes.

As a result of the polymerization, 1.6×10$^5$ g of an ethylene-hexene-1 copolymer having SCB of 22.50, [η] of 3.37, a molecular weight(Mw) of 2.9×10$^5$, a molecular weight distribution(Mw/Mn) of 23.4 and a melting point of 117.3° C. was produced per 1 mol of titanium.

Example 5

(1) Synthesis of 2-bis(2-hydroxy-3,5-dimethylphenyl)-methylthiophene

It was synthesized in the same manner as in Example 1 (1) except the use of 2,4-dimethylxylenol in place of 2-tert-butyl-4-methylphenol.

(2) Synthesis of 2,2'-(2-thienylmethylene)bis(4,6-dimethylphenoxy)titanium dichloride Under an atmosphere of argon, 0.713 g (2.0 mmol) of 2-bis(2-hydroxy-3,5-dimethylphenyl)methylthiophene and 20 ml of toluene were charged in a 50 ml Schlenk tube equipped with a stirrer, and the solution was kept at 20° C. To the solution, 0.22 ml (2.0 mmol) of titanium tetrachloride was slowly added with a syringe. The solution was continuously stirred for 12 hours. After stirring, a brick-colored solid material was precipitated. The brick-colored solid material was filtered and washed with hexane. Successively, it was dried under vacuum to obtain 0.3 g of 2,2'-(2-thienylmethylene)bis(4,6-dimethylphenoxy)titanium dichloride as a brick-colored solid material.

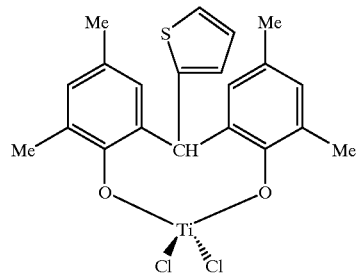

(3) Polymerization

After an autoclave having an inner volume of 400 ml and a stirrer was dried under vacuum and its atmosphere was replaced with argon, 170 ml of toluene as a solvent and 30 ml of hexene-1 as an α-olefin were charged and the temperature of the reactor was raised to 80° C. After the raise of the temperature, ethylene was fed while regulating an ethylene pressure at 6 kg/cm$^2$ and after the inner system was stabilized, 0.25 mmol of triethylaluminum was added, and successively, 5.0 μmol of 2,2'-(2-thienylmethylene)bis(4,6-dimethylphenoxy)titanium dichloride was added. Then, 15 μmol of triphenylmethyl tetrakis(pentafluorophenyl)borate was charged. While regulating the temperature at 80° C., the polymerization was carried out for 60 minutes.

As a result of the polymerization, 1.1×10$^5$ g of an ethylene-hexene-1 copolymer having SCB of 17.32, [η] of 4.67 and a melting point of 115.1° C. was produced per 1 mol of titanium.

Example 6

(1) Synthesis of 2-bis(2-hydroxy-5-methylphenol) methylthiophene

It was synthesized in the same manner as in Example 1 (1) except the use of p-cresol in place of 2-tert-butyl-4-methylphenol.

(2) Synthesis of 2,2'-(2-thienylmethylene)bis(4-methylphenoxy)titanium dichloride Under an atmosphere of argon, 0.621 g (2.0 mmol) of 2-bis(2-hydroxy-5-methylphenol)methylthiophene and 20 ml of toluene were charged in a 50 ml Schlenk tube equipped with a stirrer, and the solution was kept at 20° C. To the solution 0.22 ml (2.0 mmol) of titanium tetrachloride was slowly added with a syringe. The solution was continuously stirred for 12 hours. After stirring, a brick-colored solid material was precipitated. The brick-colored solid material was filtered and washed with hexane. Successively, it was dried under vacuum to obtain 0.2 g of 2,2'-(2-thienylmethylene)bis(4-methylphenoxy)titanium dichloride as a brick-colored solid material represented by the formula below.

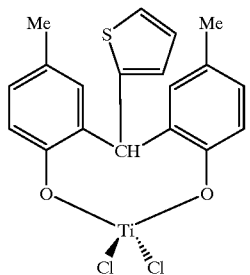

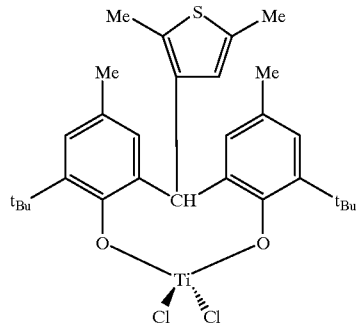

(3) Polymerization

After an autoclave having an inner volume of 400 ml and a stirrer was dried under vacuum and its atmosphere was replaced with argon, 170 ml of toluene as a solvent and 30 ml of hexene-1 as an α-olefin were charged and the temperature of the reactor was raised to 80° C. After the raise of the temperature, ethylene was fed while regulating an ethylene pressure at 6 kg/cm² and after the inner system was stabilized, 0.25 mmol of triethylaluminum was added, and successively, 5.0 μmol of 2,2'-(2-thienylmethylene)bis(4-methylphenoxy)titanium dichloride was charged. Then, 15 μmol of triphenylmethyl tetrakis(pentafluorophenyl)borate was added. While regulating the temperature at 80° C., the polymerization was carried out for 60 minutes.

As a result of the polymerization, $9.7 \times 10^4$ g of an ethylene-hexene-1 copolymer having SCB of 15.89, [η] of 5.55, a molecular weight(Mw) of $2.7 \times 10^5$, a molecular weight distribution(Mw/Mn) of 18.1 and a melting point of 123.1° C. was produced per 1 mol of titanium.

Example 7

(1) Synthesis of 3-bis(2-hydroxy-3-tert-butyl-5-methylphenyl)methyl-2,5-dimethylthiophene It was synthesized in the same manner as in Example 1 (1) except the use of 2,5-dimethyl-3-thiophenecarboxyaldehyde in place of 2-thiophenecarboxyaldehyde.

(2) Synthesis of 2,2'-(2,5-dimethyl-3-thienylmethylene)bis(6-tert-butyl-4-methylphenoxy)titanium dichloride Under an atmosphere of argon, 0.901 g (2.0 mmol) of 3-bis(2-hydroxy-3-tert-butyl-5-methylphenyl)methyl-2,5-dimethylthiophene synthesized in (1) and 30 ml of toluene were charged in a 50 ml Schlenk is tube equipped with a stirrer, and the solution was kept at 20° C. To the solution, 0.22 ml (2.0 mmol) of titanium tetrachloride was slowly added with a syringe. The solution was continuously stirred for 12 hours. After stirring, the wine-red solution obtained was concentrated and the residue was washed with hexane to obtain orange crystals by filtration. Successively, they were dried under vacuum to obtain 0.80 g of an orange solid material. The $^1$H-NMR ($C_6D_6$) data of the solid material is shown below.

δ1.47 (18H), 2.02 (6H), 2.08 (3H), 2.11 (3H), 4.99 (1H), 6.87 (1H), 6.91 (2H), 7.45 (2H)

According to the data, the orange solid material was identified as 2,2'-(2,5-dimethyl-3-thienylmethylene)bis(6-tert-butyl-4-methylphenoxy)titanium dichloride represented by the formula below.

3) Polymerization

After an autoclave having an inner volume of 400 ml and a stirrer was dried under vacuum and its atmosphere was replaced with argon, 170 ml of toluene as a solvent and 30 ml of hexene-1 as an α-olefin were charged and the temperature of the reactor was raised to 80° C. After the raise of the temperature, ethylene was fed while regulating an ethylene pressure at 6 kg/cm² and after the inner system was stabilized, 0.25 mmol of triethylaluminum was added, and successively, 5.0 μmol of 2,2'-(2,5-dimethyl-3-thienylmethylene)bis(6-tert-butyl-4-methylphenoxy)titanium dichloride was added. Successively, 15 μmol of triphenylmethyl tetrakis(pentafluorophenyl)borate was added. While regulating the temperature at 8° C., the polymerization was carried out for 30 minutes. As a result of the polymerization, $5.5 \times 10^5$ g of an ethylene-hexene-1 copolymer having SCB of 7.87, [η] of 2.72, and a melting point of 122.7° C. was produced per 1 mol of titanium.

Example 8

(1) Synthesis of 2-bis(2-hydroxy-3-tert-butyl-5-methylphenyl)methylbenzothiophene It was synthesized in the same manner as in Example 1 (1) except the use of 2-benzothiophenecarboxyaldehyde in place of 2-thiophenecarboxyaldehyde.

(2) Synthesis of 2,2'-(2-benzo[b]thienylmethylene)bis(6-tert-butyl-4-methylphenoxy)titanium dichloride Under an atmosphere of argon, 0.473 g (1.0 mmol) of 2-bis(2-hydroxy-3-tertiary-butyl-5-methylphenyl)methylbenzothiophene synthesized in (1) and 10 ml of toluene were charged in a 50 ml Schlenk tube equipped with a stirrer, and the solution was kept at 20° C. To the solution, 0.11 ml (1.0 mmol) of titanium tetrachloride was slowly added with a syringe. The solution was continuously stirred for 12 hours. After stirring, the wine-red solution obtained was concentrated and the residue was washed with hexane to obtain orange crystals by filtration. Successively, they were dried under vacuum to obtain 0.1 g of an orange solid material.

The $^1$H-NMR ($C_6D_6$) data of the solid material is shown below. δ1.50 (18H), 2.06 (6H), 6.59 (1H), 6.98 (2H), 6.99–7.10 (3H), 7.39–7.44 (2H), 7.58 (2H)

According to the data, the orange solid material was identified as 2,2'-(2-benzo[b]thienylmethylene)bis(6-tert-butyl-4-methylphenoxy)titanium dichloride represented by the formula below.

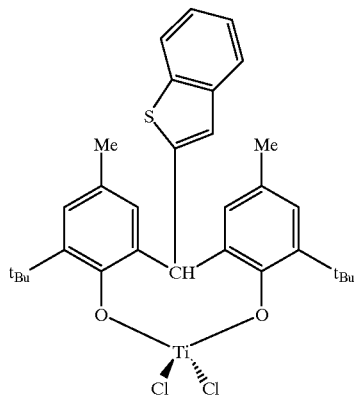

(3) Polymerization

After an autoclave having an inner volume of 400 ml and a stirrer was dried under vacuum and its atmosphere was replaced with argon, 170 ml of toluene as a solvent and 30 ml of hexene-1 as an α-olefin were charged and the temperature of the reactor was raised to 80° C. After the raise of the temperature, ethylene was fed while regulating an ethylene pressure at 6 kg/cm² and after the inner system was stabilized, 0.25 mmol of triethylaluminum was added, and successively, 5.0 μmol of 2,2'-(2-benzo[b]thienylmethylene)b is(6-tert-butyl-4-methylphenoxy) titanium dichloride was added. Then, 15 μmol of triphenylmethyl tetrakis(pentafluorophenyl)borate was added. While regulating the temperature at 80° C., the polymerization was carried out for 30 minutes. As a result of the polymerization, 2.3×10⁵ g of an ethylene-hexene-1 copolymer having SCB of 17.33 and [η] of 2.22 was produced per 1 mol of titanium and 1 hour.

Example 9

(1) Synthesis of 2-bis(2-hydroxy-3-tert-butyl-5-bromophenyl)methylthiophene

It was synthesized in the same manner as in Example 1 (1) except the use of 2-tert-butyl-4-bromophenol in place of 2-tert-butyl-4-methylphenol.

(2) Synthesis of 2,2-(2-thienylmethylene)bis(6-tert-butyl-4-bromophenoxy)titanium dichloride Under an atmosphere of argon, 1.10 g (2.0 mmol) of 2-bis(2-hydroxy-3-tert-butyl-5-bromophenyl) methylthiophene synthesized in (1) and 20 ml of toluene were charged in a 50 ml Schlenk tube equipped with a stirrer, and the solution was kept at 20° C. 0.22 ml (2.0 mmol) of titanium tetrachloride was slowly added to the solution by using a syringe. The solution was continuously stirred for 12 hours. After stirring, an orange solid material was precipitated. The orange solid material was filtered and washed with hexane. Successively, it was dried under vacuum to obtain 0.31 g of the orange solid material.

The ¹H-NMR (C₆D₆) data of the solid material is shown below. δ1.26 (18H), 6.26 (1H), 6.55 (1H), 6.69 (2H), 7.33 (2H), 7.86 (2H)

According to the data, the orange solid material was identified as 2,2-(2-thienylmethylene)bis(6-tert-butyl-4-bromophenoxy)titanium dichloride represented by the formula below.

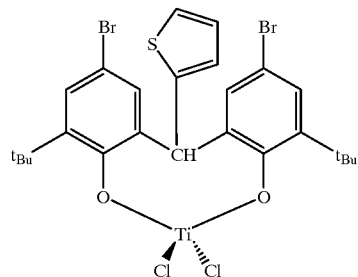

(3) Polymerization

After an autoclave having an inner volume of 400 ml and a stirrer was dried under vacuum and its atmosphere was replaced with argon, 170 ml of toluene as a solvent and 30 ml of hexene-1 as an α-olefin were charged and the temperature of the reactor was raised to 80° C. After the raise of the temperature, ethylene was fed while regulating an ethylene pressure at 6 kg/cm² and after the inner system was stabilized, 0.25 mmol of triisobutylaluminum was added, and successively, 5.0 μmol of 2,2-(2-thienylmethylene)bis (6-tert-butyl-4-bromophenoxy)titanium dichloride was added. Successively, 15 μmol of triphenylmethyl tetrakis (pentafluorophenyl)borate was added. While regulating the temperature at 80° C., the polymerization was carried out for 30 minutes. As a result of the polymerization, 1.4×10⁵ g of an ethylene-hexene-1 copolymer having SCB of 32.97 and [η] of 2.70 was produced per 1 mol of titanium and 1 hour.

Example 10

(1) Synthesis of 2-bis(2-hydroxy-3-tert-butyl-5-methoxyphenyl)methylthiophene

It was synthesized in the same manner as in Example 1 (1) except the use of 2-tert-butyl-4-methoxyphenol in place of 2-tert-butyl-4-methylphenol.

(2) Synthesis of 2,2-(2-thienylmethylene)bis(6-tert-butyl-4-methoxyphenoxy)titanium dichloride Under an atmosphere of argon, 0.91 g (2.0 mmol) of 2-bis(2-hydroxy-3-tert-butyl-5-methoxyphenyl) methylthiophene synthesized in (1) and 20 ml of toluene were charged in a 50 ml Schlenk's tube equipped with a stirrer, and the solution was kept at 20° C. To the solution, 0.22 ml (2.0 mmol) of titanium tetrachloride was slowly added with a syringe. The solution was continuously stirred for 12 hours. After stirring, a dark brown solid material was precipitated. The dark brown solid material was filtered and washed with hexane. Successively, it was dried under vacuum to obtain 0.3 g of the dark brown solid material.

The ¹H-NMR (C₆D₆) data of the solid material is shown below. δ1.44 (18H), 3.28 (6H), 6.57 (1H), 6.66 (1H), 6.80 (3H), 6.92 (1H), 7.29 (2H)

According to the data, the dark brown solid material was identified as 2,2-(2-thienylmethylene)bis(6-tert-butyl-4-methoxyphenoxy)titanium dichloride represented by the formula below.

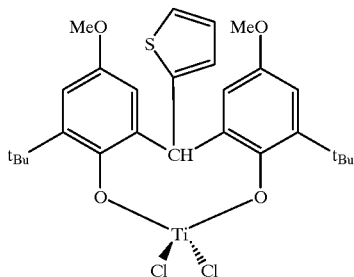

(3) Polymerization

After an autoclave having an inner volume of 400 ml and a stirrer was dried under vacuum and its atmosphere was replaced with argon, 170 ml of toluene as a solvent and 30 ml of hexene-1 as an α-olefin were charged and the temperature of the reactor was raised to 80° C. After the raise of the temperature, ethylene was fed while regulating an ethylene pressure at 6 kg/cm$^2$ and after the inner system was stabilized, 0.25 mmol of triisobutylaluminum was added, and successively, 5.0 μmol of 2,2-(2-thienylmethylene)bis(6-tert-butyl-4-methoxyphenoxy)titanium dichloride was added. Then, 15 μmol of triphenylmethyl tetrakis(pentafluorophenyl)borate was added. While regulating the temperature at 80° C., the polymerization was carried out for 30 minutes. As a result of the polymerization, 6.9×10$^5$ g of an ethylene-hexene-1 copolymer having SCB of 23.04, [η] of 1.15 and a melting point of 100.4° C. was produced per 1 mol of titanium and 1 hour. The results of the above-mentioned Examples and Comparative Examples were collectively shown in Tables 1.

TABLE 1

| | Activity g/molTiHr | SCB | [η] | Melting point °C. |
|---|---|---|---|---|
| Example 1 | 1.7 × 10$^6$ | 19.8 | 1.61 | 107.4 |
| Example 2 | 4.7 × 10$^5$ | 19.20 | 1.26 | |
| Example 3 | 2.4 × 10$^5$ | 34.64 | 3.23 | |
| Example 4 | 1.6 × 10$^5$ | 22.50 | 3.37 | 117.3 |
| Example 5 | 1.1 × 10$^5$ | 17.32 | 4.67 | 115.1 |
| Example 6 | 9.7 × 10$^4$ | 15.89 | 5.55 | 123.1 |
| Example 7 | 5.5 × 10$^5$ | 7.87 | 2.72 | 122.7 |
| Example 8 | 2.3 × 10$^5$ | 17.33 | 2.22 | |
| Example 9 | 1.4 × 10$^5$ | 32.97 | 2.70 | |
| Example 10 | 6.9 × 10$^5$ | 23.04 | 1.15 | |
| Comparative Example | 2.9 × 10$^4$ | 26.1 | 3.78 | 116.8 |

Example 11

(1) Synthesis of bis(2-hydroxy-3-tert-butyl-5-methylphenyl)(4-methoxyphenyl)phosphine In an atmosphere of nitrogen, 10.41 g(50 mmol) of 2-tert-butyl-4-methylphenol was dissolved in 100 ml of tetrahydrofuran diethyl ether and 31.1 ml of n-butyl lithium (1.6M n-hexane solution) was added dropwise to this solution at −78° C. Thereafter, the temperature was elevated to room temperature and the reaction-mixture was stirred for 12 hours. 10 ml of hexamethylphosphoric triamide was added to the the resulting slurry for obtaining a homogenous solution, and then, after cooled to −78° C., 5.22 g(25 mmol) of dichloro(methoxyphenyl)phosphine was added. Subsequently, after elevating to room temperature, the solution was refluxed for 30 minutes. After natural cooling, 100 ml of water was added to terminate the reaction and then an extracting treatment was carried out using toluene (100 ml, three times). The organic layer was washed with a saturated aqueous sodium hydroxide solution and was dried with anhydrous sodium sulfate, and then the solvent was distilled off. The residue was purified by a silicagel column chromatography (a developing solvent: hexane/ethyl acetate=30/1) to obtain bis(2-hydroxy-3-tert-butyl-5-methylphenyl)(4-methoxyphenyl)phosphine of colorless crystal with the yield of 14%. The melting point was 122.5–123.5° C.

The $^1$H-NMR spectrum data of the compound is shown below. δ1.38(s,18H), 2.18(s,6H), 3.81(s,3H), 6.16(d,2H, J=8.6, 1.3 Hz), 6.67(dd,2H,J=6.3,1.7 Hz), 6.88(dd,2H,J=8.6, 1.3 Hz), 7.13(d,2H, J=1.7 Hz), 7.24(dd,2H,J=8.6,8.6 Hz)

(2) Synthesis of 2,2'-(4-methoxyphenylphosphine)bis(6-tert-butyl-4-methylphenoxy)titanium dichloride Under an atmosphere of argon, to a solution of 0.233 g (0.5 mmol) of 2-bis(2-hydroxy-3-tert-butyl-5-methylphenyl)methylphosphine synthesized in (1) dissolved in 10 ml of toluene, 0.33 ml of 3M methyl magnesium bromide diethyl ether solution was added dropwise and the reaction mixture was continuously stirred for 12 hours. The reaction liquid was cooled to −78° C., and subsequently 0.5 ml of 1M titanium tetrachloride toluene solution was added dropwise. After elevating to room temperature, further the reaction mixture was continuously stirred for 12 hours. Thus obtained mixture was filtered to eliminate a toluene-insoluble matter and the solution obtained was concentrated to obtain 0.206 g of a brick-color solid material.

(3) Polymerization

After an autoclave having an inner volume of 400 ml and a stirrer was dried under vacuum and its atmosphere was replaced with argon, 170 ml of toluene as a solvent and 30 ml of hexene-1 as an α-olefin were charged and the temperature of the reactor was raised to 80° C. After the raise of the temperature, ethylene was fed while regulating an ethylene pressure at 6 kg/cm$^2$ and after the inner system was stabilized, 0.25 mmol of triethylaluminum was charged, and then, 5.0 μmmol of 2,2'-(4-methoxyphenylphosphine)bis(6-tert-butyl-4-methylphenoxy)titanium dichloride was charged. Successively, 15 μmol of triphenylmethyl tetrakis(pentafluorophenyl)borate was charged. While regulating the temperature at 80° C., the polymerization was carried out for 30 minutes.

As a result of the polymerization, 2.2×10$^6$ g of an ethylene-hexene-1 copolymer having SCB of 32.7, [η] of 0.68 and a melting point of 99.8° C. was produced per 1 mol of titanium and an hour.

As described above in detail, according to the present invention, there is provided a transition metal complex having a cyclic structure where two oxygen atoms are bonded with the transition metal, further containing a hetero atom in a substituent group not contained in the cyclic structure and having an excellent thermal stability.

An olefin polymer having a high molecular weight and a narrow composition distribution; particularly a linear low density polyethylene can be efficiently produced at an industrially advantageous reaction temperature with an olefin polymerization catalyst wherein the said complex is a main catalyst component for polymerizing an olefin. Besides, the amount used of aluminoxane which is expensive and must be used in a large amount can be reduced.

What is claimed is:

1. A process for producing an olefin polymer which comprises polymerizing an α-olefin or copolymerizing two kinds or more of α-olefins with an olefin polymerization catalyst using an olefin polymerization catalyst component represented by the general formula (1):

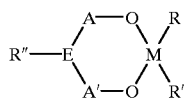
(1)

wherein M is the transition metal element of the $4^{th}$ Group or the Lanthanide Series in the Periodic Table; each of A and A' is the same or different and is a hydrocarbon or halogenated hydrocarbon having 1 to 50 carbon atoms, or a hydrocarbon or halogenated hydrocarbon group having 1 to 50 carbon atoms and a substituent containing an oxygen atom; E is a residual group of an element of the $13^{th}$, $14^{th}$ or $15^{th}$ groups capable of forming bonds at three positions; each of R and R' is the same or different and is a halogen atom or a hydrocarbon group having 1 to 20 carbon atoms; R" represents a hydrocarbon or halogenated hydrocarbon group containing at least one hetero atom and having 1 to 20 carbon atoms; and a composition (A) described below:
(A) any of compounds (A1) to (A3) below or an admixture of two or three compounds thereof; wherein
(A1) is an organoaluminum compound indicated by the general formula $R^1_a AlX_{3-a}$,
(A2) is a cyclic aluminoxane having a structure indicated by the general formula $\{-Al(R^2)-O-\}_b$, and
(A3) is a linear aluminoxane having a structure indicated by the general formula $R^3(R^3-Al-O)_c AlR^3_2$, wherein each of $R^1$, $R^2$ and $R^3$ is the same or different and is a hydrocarbon group having 1 to 8 carbon atoms; X represents a hydrogen atom or a halogen atom and may represent two or more different atoms; a is a number satisfying $0 < a \leq 3$, b represents an integer of 2 or more and c represents an integer of 1 or more.

2. A process for producing an olefin polymer according to claim 1, wherein said olefin polymerization catalyst further comprises a compound (B) selected from the group consisting of boron compounds (B1) represented by the general formula $BQ^1Q^2Q^3$; boron compounds (B2) represented by the general formula $Z^+(BQ^1Q^2Q^3Q^4)^-$; and boron compounds (B3) represented by the general formula $(L-H)^+ (BQ^1Q^2Q^3Q^4)^-$, wherein $Z^+$ is a cationic oxidizing agent, each of $Q^1$, $Q^2$, $Q^3$ and $Q^4$ is the same or different and is a halogen atom, a hydrocarbon group having 1 to 20 carbon atoms, a halogenated hydrocarbon group having 1 to 20 carbon atoms, a silyl group having 1 to 20 carbon atoms, an alkoxy group having 1 to 20 carbon atoms, or an amide group having 1 to 20 carbon atoms, and $(L-H)^+$ is a Brønsted acid.

3. A process for producing an olefin polymer according to claim 1, wherein said olefin polymer [ia] is an ethylene-α-olefin copolymer.

4. A process for producing an olefin polymer according to claim 2, wherein said olefin polymer [ia] is an ethylene-α-olefin copolymer.

* * * * *